US010568725B2

(12) United States Patent
Sedic (10) Patent No.: US 10,568,725 B2
(45) Date of Patent: Feb. 25, 2020

(54) TOOTHBRUSH WITH BIOFILM-REMOVING TOUCH POINTS (71) Applicant: Filip Sedic, Shanghai (CN)

(72) Inventor: Filip Sedic, Shanghai (CN)

(73) Assignee: FOREO Inc., Las Vegas, NV (US)

( * ) Notice: Subject to any disclaimer, the term of this patent is extended or adjusted under 35 U.S.C. 154(b) by 380 days.

(21) Appl. No.: 15/402,413

(22) Filed: Jan. 10, 2017

(65) Prior Publication Data

US 2017/0128179 A1 May 11, 2017

Related U.S. Application Data (63) Continuation of application No. 14/576,134, filed on Dec. 18, 2014, now Pat. No. 9,578,956.

(Continued)

(51) Int. Cl.
*A61C 17/34* (2006.01)
*A46D 1/00* (2006.01)
(Continued)

(52) U.S. Cl.
CPC .......... *A61C 17/3481* (2013.01); *A46B 9/028* (2013.01); *A46B 9/04* (2013.01);
(Continued)

(58) Field of Classification Search
CPC ... A61C 17/3481; A61C 17/22; A61C 17/222; A61C 17/225; A46B 9/028; A46B 9/04; A46B 13/023; A46D 1/0207
See application file for complete search history.

(56) References Cited

U.S. PATENT DOCUMENTS 659,593 A 10/1900 Richards
1,327,757 A 1/1920 Eggers
(Continued)

FOREIGN PATENT DOCUMENTS

CN 3594120 1/2007
CN 201070108 6/2008
(Continued)

OTHER PUBLICATIONS

State Intellectual Property Office of the People's Republic of China, First Office Action, Chinese Pat. App. No. 20140068758.7, dated Feb. 4, 2017, 13 pages.
(Continued)

*Primary Examiner* — Shay Karls
(74) *Attorney, Agent, or Firm* — Evan Feldstein (57) ABSTRACT A tooth brush device having bristle touch-points composed of a polymer material (e.g., silicone) provides improved biofilm removal from teeth. The tooth brush device comprises a head with an apex, a base opposite the apex, a front surface, and a back surface opposite the front surface. The front surface of the head includes bristle touch-points arranged along rows. The rows are arranged orthogonal to the longitudinal axis of the head extending from the apex of the head to the base of the head. Each of a plurality of the bristle touch-points is a single solid elongate structure extending from the head and is composed of a polymer material. The device further includes a neck coupled to the base of the head and a handle coupled to the head via the neck.

17 Claims, 10 Drawing Sheets

Related U.S. Application Data (60) Provisional application No. 61/919,673, filed on Dec. 20, 2013.

(51) Int. Cl.
*A61C 17/22* (2006.01)
*A46B 9/04* (2006.01)
*A46B 13/02* (2006.01)
*A46B 9/02* (2006.01)
*A61C 17/16* (2006.01)

(52) U.S. Cl.
CPC .......... *A46B 13/023* (2013.01); *A46D 1/0207* (2013.01); *A61C 17/22* (2013.01); *A61C 17/222* (2013.01); *A61C 17/225* (2013.01); *A46B 2200/1026* (2013.01); *A46B 2200/1066* (2013.01); *A61C 17/16* (2013.01)

(56) References Cited

U.S. PATENT DOCUMENTS

| | | | |
|---|---|---|---|
| D59,127 S | 9/1921 | Perrault | |
| 2,225,331 A | 12/1940 | Campbell | |
| 3,734,106 A | 5/1973 | Zimmerman | |
| D402,116 S | 12/1998 | Magloff et al. | |
| 5,956,796 A | 9/1999 | Lodato | |
| D419,774 S | 2/2000 | Langue | |
| D444,303 S | 7/2001 | Reille | |
| 6,357,074 B1 * | 3/2002 | Weihrauch | A46B 5/0025 15/167.1 |
| 6,490,760 B1 | 12/2002 | Lauer et al. | |
| D503,852 S | 4/2005 | Hensel | |
| 6,955,539 B2 * | 10/2005 | Shortt | A61C 17/34 132/322 |
| D536,452 S | 2/2007 | Geiberger et al. | |
| 7,360,269 B2 * | 4/2008 | Cobabe | A46B 5/0075 15/22.1 |
| D578,772 S | 10/2008 | Provost et al. | |
| D611,254 S | 3/2010 | Lee | |
| D617,563 S | 6/2010 | Wagner | |
| D639,068 S | 6/2011 | Cobabe et al. | |
| D669,687 S | 10/2012 | Heil et al. | |
| D676,662 S | 2/2013 | Jimenez et al. | |
| 8,549,693 B2 | 10/2013 | Gruber et al. | |
| D693,581 S | 11/2013 | Ballmaier et al. | |
| D694,524 S | 12/2013 | Erskine-Smith | |
| D696,023 S | 12/2013 | Gebski | |
| D696,517 S | 12/2013 | Gebski | |
| D710,109 S | 8/2014 | Nanda | |
| D717,547 S | 11/2014 | Adriaenssen et al. | |
| 2003/0037391 A1 | 2/2003 | Pfenniger et al. | |
| 2003/0046780 A1 | 3/2003 | Davis | |
| 2005/0241091 A1 | 11/2005 | Foster et al. | |
| 2006/0064833 A1 | 3/2006 | Jacobs | |
| 2007/0050931 A1 | 3/2007 | Jimenez et al. | |
| 2007/0251034 A1 | 11/2007 | Meressa et al. | |
| 2008/0196184 A1 | 8/2008 | Dooley | |
| 2010/0024143 A1 | 2/2010 | Dickie | |
| 2010/0269275 A1 | 10/2010 | Shimoyama et al. | |
| 2011/0010874 A1 | 1/2011 | Dickie | |
| 2011/0151404 A1 | 6/2011 | Dombrowski | |
| 2013/0061412 A1 | 3/2013 | Vashi | |
| 2014/0259469 A1 | 9/2014 | Garrigues et al. | |
| 2014/0261538 A1 | 9/2014 | Elseri | |
| 2016/0175154 A1 | 6/2016 | Olson | |

FOREIGN PATENT DOCUMENTS

| | | | |
|---|---|---|---|
| CN | 301855900 | 3/2012 | |
| CN | 302002637 | 7/2012 | |
| DE | 40400262-0006 | 5/2004 | |
| EP | 2328437 | 4/2016 | |
| FR | 2909532 | 6/2008 | |
| JP | 2002-514946 | 5/2002 | |
| JP | 2003153741 A * | 5/2003 | |
| JP | 2006-521833 | 9/2006 | |
| JP | 2008-80140 | 4/2008 | |
| JP | 2009-136615 | 6/2009 | |
| JP | 2010-51795 | 3/2010 | |
| JP | 2010-274079 | 12/2010 | |
| KR | 10-2012-0026955 | 3/2012 | |
| WO | WO2005096882 | 10/2005 | |
| WO | WO-2011013533 A1 * | 2/2011 | A46B 9/04 |

OTHER PUBLICATIONS

IP Australia, "Examination report No. 1 for standard patent application," dated Dec. 19, 2018, pp. 1-2.
PCT International Search Report and Written Opinion, PCT Application No. PCT/IB2014/003193, dated Jun. 18, 2015, 10 pages.
USPTO_"Non-final Office Action," dated May 23, 2016, pp. 1-7.
Applicant_Response to Office Action dated May 23, 2016, filed Aug. 8, 2016, pp. 1-10.
EPO, "Supplementary European Search Report" for Int. App. No. 14872403.2, dated Jul. 7, 2017, pp. 1-8.
Japanese Patent Office, "Official Notice of Rejection," Japanese patent No. 2016-541186, dated Nov. 27, 2018, pp. 1-11.
Applicant's Response to First Office Action issued by State Intellectual Property Office of the People's Republic of China, filed May 27, 2017, pp. 1-8 (with English translation).
KIPO, "First Office Action," International app. No. 10-2016-7019434, dated Sep. 30, 2019, pp. 1-6.

* cited by examiner

TOOTHBRUSH WITH BIOFILM-REMOVING TOUCH POINTS

CROSS-REFERENCE To RELATED APPLICATION

This application is a continuation of U.S. Non-provisional patent application Ser. No. 14/576,134, filed Dec. 18, 2014, which claims the benefit of U.S. Provisional Application Ser. No. 61/919,673, filed Dec. 20, 2013. Each of these related applications is incorporated by reference into this disclosure in its entirety.

BACKGROUND

The disclosure relates generally to a toothbrush, and more particularly to tooth cleaning, and gum muscle and tissue massage, stimulation, or treatment that combines specific geometry, material properties and stimulation generated by one or more motors of the toothbrush apparatus.

General mouth hygiene and oral health is dependent on the presence of microbial cultures and bacteria on the teeth, and in the mouth cavity, and the related microbial excretions that damage the protective layers of teeth causing greater probability of cavity creation and development. These microbial cultures are present in the biofilm on the surfaces of the teeth and in the food that remains present in the oral cavity and on the surfaces of the teeth. Effective removal of biofilm and food diminishes the presence of microbial cultures and excretions, and aids to improve the natural protection of teeth, leading to better oral hygiene.

The gum tissue and muscles are vital for the protection of the teeth as far as exposure of the lower layers of the teeth and sensitivity to touch and temperature changes are concerned. Today's dental care products and toothbrush apparatus rely on the use of nylon bristles that can, in the case of application of too much pressure, damage the gum tissue and muscles. In addition, today's dental care apparatuses and toothbrushes that are based on nylon or equivalent bristles do not stimulate the tissue nor enhance circulation important for the regenerative and continuous healing process of the gum tissue and muscles.

To date, the devices to address oral hygiene are based on nylon bristles that are designed to reduce the presence of biofilm, remove food remains, and treat gum tissue and muscles, however these devices are not very effective due to the geometry and properties of the bristles, which limits their ability to remove the very thin biofilm across large surface areas of the teeth. These bristles also fail to effectively stimulate gum tissue and muscles. In fact, most devices currently available are designed with special mechanisms to minimize damage to the gum tissue rather than to stimulate gum tissue. What is needed, therefore, is a device that would overcome the above limitations and both remove the biofilm with greater efficacy while stimulating gum tissue and muscles effectively and safely.

SUMMARY

Embodiments include a toothbrush apparatus with one or more oscillating motors, or other electromagnetic devices that can provide the toothbrush with various frequency pulsations, and an exterior that can be composed of a soft elastic material, such as silicone. The apparatus also includes a brush with one or more textured surfaces including touch-points of, for example, 0.5 to 2.5 mm in dimension, or solid surfaces with ridges for cleaning the teeth and interacting with the gum tissue and muscles. The oscillating motor moves or oscillates the textured surfaces of the brush for application to a user's teeth and gums. As the user moves the toothbrush on the teeth and gums, the oscillating pulsations combined with the textured surfaces' touch-points remove biofilm and other contaminants on the tooth surface. The oscillating pulsations provide a tapping motion to the user's gums to stimulate the tissue without abrasive action. The oscillations occur at around 50-300 Hertz (Hz). One embodiment includes a high-frequency and a low-frequency oscillating motor, or other electromagnetic device, that may operate simultaneously. The simultaneous pulsations provide a deep cleaning to the teeth. While referred to here as a toothbrush, the device can also perform other functions besides cleaning, including massaging, stimulating, heating, applying tooth paste or other substances, and so forth.

The figures depict various embodiments of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Figure 1:
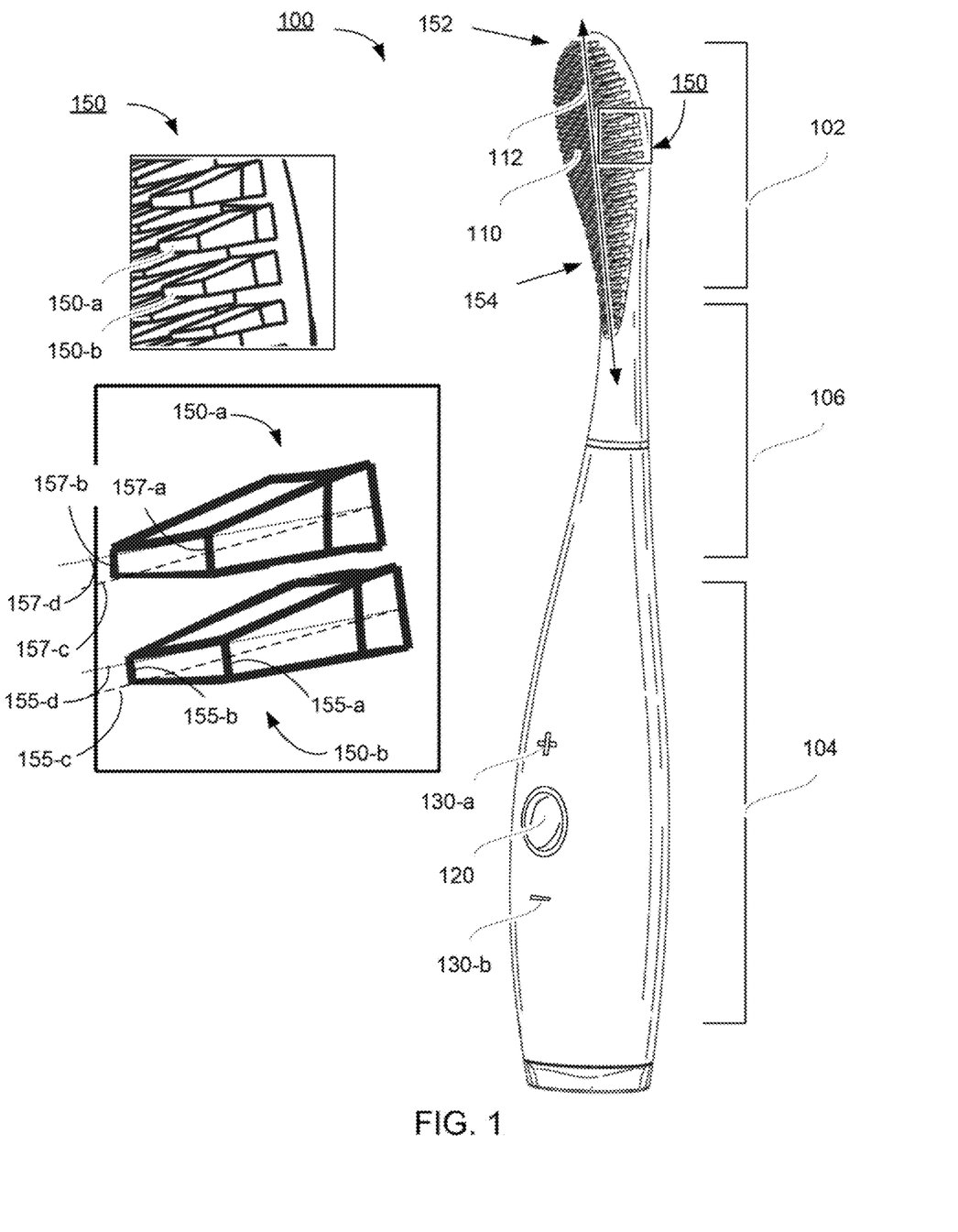
FIG. 1 is a perspective view of a toothbrush, according to one embodiment.

FIG. 1 is a perspective view of a toothbrush 100, according to one embodiment. In some embodiments, the toothbrush 100 is an electromechanical device that uses electric power from AC mains (e.g., through a power converter) or uses battery power and generates mechanical energy to mechanically stimulate and provide pulsations to various parts of the mouth (teeth, gums, gumline, jaws, tongue, inner cheek walls, and the like).

As shown in FIG. 1, toothbrush 100 has a head 102, a handle 104, and a neck 106. Neck 106 couples or connects the head 102 to the handle 104. Depending on the use case or application, and depending on the target users (e.g., children versus adults, people with sensitive teeth or gums, and so on), toothbrush 100 can be made of a variety of different materials, a variety of different sizes (e.g., smaller tooth brushes for children), such as different overall lengths, different lengths or widths of head 102, different lengths or widths of the handle 104, and so on. Head 102 optionally has a rounded or smooth perimeter and tapers toward the apex (e.g., in an oval shape), thereby facilitating easier usage in the mouth.

In some embodiments, a front surface of the head 102 includes bristle touch-points 110 arranged along rows. The rows in turn are arranged orthogonally to a longitudinal axis 112 of the head 102 extending from an apex 152 of the head 102 to the base 154 of the head 102.

In some embodiments, as illustrated in the inset 150, a given bristle touch-point of the plurality of bristle touch-points is a single solid elongate structure. Furthermore, as shown in inset 150, the single solid elongate structure of a given bristle touch-point has rectangular or substantially rectangular cross-sections of decreasing cross-sectional area from a proximal end to a distal end of the given bristle touch-point. In other words, the single solid elongate structure of a given bristle touch-point tapers along its central axis from a base to a tip, forming a frustum of a rectangular pyramid. In some embodiments, the elongate structure of a bristle touch-point has a polygonal cross-section. For example, the cross-section may be trapezoidal—two parallel sides of the trapezoid cross-section formed parallel to the longitudinal axis of the head, the side closer to a lateral or outer edge of the head having a greater length than the side further away from the lateral or outer edge of the head. This is illustrated in the view 160 where touch-points 150-*a* and 150-*b* of the inset 150 have trapezoidal cross sections. The sides of the trapezoid closer to the outer edge or periphery of the tooth brush head (e.g., 155-*a* and 157-*a*) have a greater dimension than the side of the trapezoid further away from the periphery (e.g., 155-*b* and 157-*b*). Thus, the touch-points may be designed to be wider in cross-section near the outer edge of the brush head and narrower in cross section toward the center. This variation or difference in width (e.g., the difference between length of side 155-*a* and length of side 155-*b*) for an individual touch point may be greater for the touch points that are closer to the outer or lateral periphery of the head. In such embodiments, the touch points near the center of the brush head are more rectangular and have more uniform widths. Other cross-sectional shapes such as circular, oval, oblong, concave shapes may be used alternatively or in addition to the polygonal shapes. Cross sectional shapes may also vary based on a location of the touch point on the head of the tooth brush—for example, circular cross sections may be used for touch points near the apex 152, trapezoidal cross sections near the outer periphery of the head, and rectangular or square cross sections may be used in the central region of the head.

Moreover, the cross-sectional shapes may be configured to have a narrower or smaller dimension along the longitudinal axis of the tooth brush head. For example, the narrower or shorter sides of the rectangular or polygonal cross section are optionally parallel to the longitudinal axis of the tooth brush head. In the illustration of touch points 150-*a* and 150-*b*, the shorter sides 155-*a* and 155-*b* are formed parallel to or along the longitudinal axis of the tooth brush head. This design feature results in less resistance to flexure or bending forces that are applied along the longitudinal axis of the tooth brush head than along a lateral, short, or horizontal axis of the tooth brush head. More generally, a width of the touch points may be increased or greater along a direction orthogonal to a direction in which the brush strokes or flexure forces are likely to be applied, thus providing lower resistance to these flexure forces.

In some embodiments, a center of the touch-point cross section aligns with the central axis of the touch-point throughout the length of the touch-point—in other words, the bristle touch point tapers along its central axis. In this case, the central axis of the touch point is orthogonal to the plane of the base of the touch point where the touch point contacts or is attached to the head of the tooth brush. This centered tapering provides symmetric mechanical flexure properties along the central axis of the touch point. Alternatively, a center of the touch-point cross section may be offset relative to the central axis of the touch-point as the touch-point tapers along its length. In other words, the bristle touch-point may asymmetrically taper away from the central axis and the axis of tapering may be offset and angled (e.g., non-parallel) to the central axis of the touch-point. This is illustrated in the views of touch points 150-*a* and 150-*b* where the axes of tapering 155-*c* and 157-*c* are offset or angled relative to the central axes 155-*d* and 157-*d* of the touch points. This non-centered centered tapering may be used to provide asymmetric mechanical flexure properties to forces applied from opposite sides of the central axis of the touch point. For example, if the bristle touch-points (e.g., touch points 150-*a* and 150-*b*) taper towards a base side of the tooth brush head, as illustrated in FIG. 1, then the bristle touch points offer more flexibility (less resistance) to flexing or bending toward the base 154 of the tooth brush head than towards the apex 152 of the head.

More generally, an axis of tapering of the touch points may be angled away from a central axis of the touch point in a direction in which flexure forces associated with brush strokes are likely to be applied. The measure of the angle formed between the central axis and the axis of tapering may vary with the measure of asymmetry that is desired between the amount of resistance to be applied to flexure forces in the two opposite directions. In such embodiments, this differential resistance to brush strokes in opposite directions provides differential levels of cleansing. For example, referring to the angled bristle touch points 150-*a* and 150-*b* of FIG. 1, brush strokes that bend the touch points toward the apex (bend upwards) would face greater resistance and cause firmer or stronger cleansing than brush strokes that bend the touch points toward the base (bend downwards). Strokes along the latter direction would face lower resistance and provide gentler cleansing. The measure of the angle formed between the central axis and the axis of tapering may also vary across touch points—some touch points may have a more symmetric tapering than others. This variation in the measure of the angle may vary based on locations of the touch points on the brush head.

In some embodiments, the single solid elongate structure of the bristle touch-point is composed of a polymer material (such as silicone). In some embodiments, a Young's modulus of the polymer material ranges approximately from 0.001 GPa to 0.05 GPa. In some embodiments, the Young's modulus of the polymer material ranges approximately from 0.01 GPa to 0.1 GPa. In some embodiments, a Young's modulus of the polymer material is lower than a specified threshold (e.g., less than 0.1 GPa or less than 1 GPa, and so on).

A polymer material having such mechanical properties is typically softer, less rigid, and more malleable (flexible or pliable) than other materials, such as nylon or polypropylene, which typically have a higher Young's modulus (e.g., commonly in the 2-4 GPa range for nylon, 1.5-2 GPa for polypropylene, and so on). As a result, the bristle touch-points made from such polymer materials (as silicone) are gentle on the mouth parts and do not damage or injure the mouth parts (such as gums and other soft tissue of the mouth) during brushing or mechanical stimulation. Accordingly, the touch-points described herein are gentler than bristles used in conventional toothbrushes, thereby providing better comfort and functionality for children, for people with sensitive teeth, for people with dental conditions, such as receding gum lines, for aggressive brushers, and the like.

It should be understood that although the Young's modulus is described and used herein as one metric for illustrating the mechanical properties of the materials that can be used for making the bristle touch-points, other metrics (e.g., other moduli of elasticity such as shear modulus or bulk modulus; tensile strength, compressive strength, modulus of resilience, and so on) may alternatively be used to select an appropriate material that has these desired mechanical properties—e.g., has the desired softness, is adequately pliable, offers the desired range of resistance to being deformed elastically (e.g., non-permanently) when a force is applied to it, and has the desired resilience to restore its original shape once the force is removed. The Young's modulus is just one example of such a metric or mechanical parameter.

Additionally, mechanical properties that relate to the shapes or structures of the bristle touch-point may be defined or specified in addition to or instead of the mechanical properties of the material of which the touch-points are made. Such structural or shape dependent properties may be defined in terms of ranges of a bending modulus, a flexural modulus, and the like. Although the ranges of each of these parameters is not specifically listed here, it should be understood that any suitable parameters may be used to select a material that in combination with the shape or structure described herein provides these desired material properties.

Furthermore, silicone is characterized by stronger adhesive properties (tendency to adhere or stick to surfaces) than several other materials, such as nylon. Thus, bristle touch-points made of polymers, such as silicone, form a stronger mechanical bond with biofilms in the mouth and provide improved friction or drag forces that help clean the biofilms effectively from tooth surfaces. The shape of the bristle touch-points also assists in removing biofilm. The elongated, thin, generally flat surfaces of the touch-points cover at least 50% and some cases 100% of one of the tooth surfaces, and are dragged across the surface of the tooth during brushing to cleanse or polish the tooth.

Additionally, a hygienic silicone material that is fast-drying and non-absorbent can be used, thus allowing the tooth brush 100 to be used in the mouth and in water-based media and environments. Such a material is also easy to clean with water and even with soap or other cleansers as needed and is readily dryable after cleaning, unlike nylon bristles that tend to absorb and retain water and cleansers.

Additionally, the filaments of conventional nylon bristles commonly flex, deform, and spread out around the outer edges (lateral peripheries of the front surface of the head) due to long term use of the tooth brush resulting in the bristles becoming ineffective or less effective for prolonged or long-term use. Additionally, upon undergoing such permanent deformation, such bristles become potentially hurtful or harmful on the gums and soft tissues of the mouth. In contrast, the thicker silicone bristle touch-points, being more flexible, elastic, and thicker, are more resistant to mechanical wear, permanent flexure, or deformation. In some embodiments, the touch-points are thinner along the direction of brush strokes (e.g., along the longitudinal axis of the tooth brush) and therefore are less likely to undergo flexure in an orthogonal direction to the direction of brush strokes or brushing action. Thus, the touch-points are more immune to permanently outwardly deforming or bending out of shape along the outer edges or lateral peripheries of the toothbrush head.

In some embodiments, the toothbrush 100 also includes manual controls 120, 130-a, and 130-b that enable the user to vary one or more parameters or attributes of the mechanical stimulation energy provided to the mouth by the vibration of the brush head. For example, the controls 120, 130-a, and 130-b may be used to modify (e.g., increase 130-a or decrease 130-b) a frequency of mechanical vibrations provided to various mouth parts. As another example, the controls 120, 130-a, and 130-b may be used to modify (e.g., increase or decrease) an intensity (e.g., amplitude or strength) of mechanical vibrations provided to various mouth parts. As yet another example, the controls 120, 130-a, and 130-b may be used to modify a direction (e.g., longitudinal or lateral rubbing, vertical tapping, circular or rotatory direction) of mechanical vibrations provided to various mouth parts. As yet another example, the controls 120, 130-a, and 130-b may be used to modify a pattern (e.g., burst mode pattern, continuous pattern, preprogrammed combination of frequency and intensity patterns) of mechanical vibrations provided to various mouth parts. The user may increase or decrease a parameter value (e.g., intensity or frequency) of vibration of the motor through the manual controls to set an appropriate parameter value desired by the user. The parameter value set by the user may be stored by a controller (that controls or governs the operation of the brush) when the controller is deactivated, such that the next time the controller is turned on, the controller resumes operation the desired parameter value. Manual controls 120, 130-a, and 130-b are optionally placed along the handle 104 (which also serves as a hand grip) for convenient access and use. Alternatively, or in addition, in some embodiments, the one or more parameters or attributes of the mechanical stimulation energy provided to the mouth by the vibration of the brush head may be varied through a wireless remote.

Figure 2:
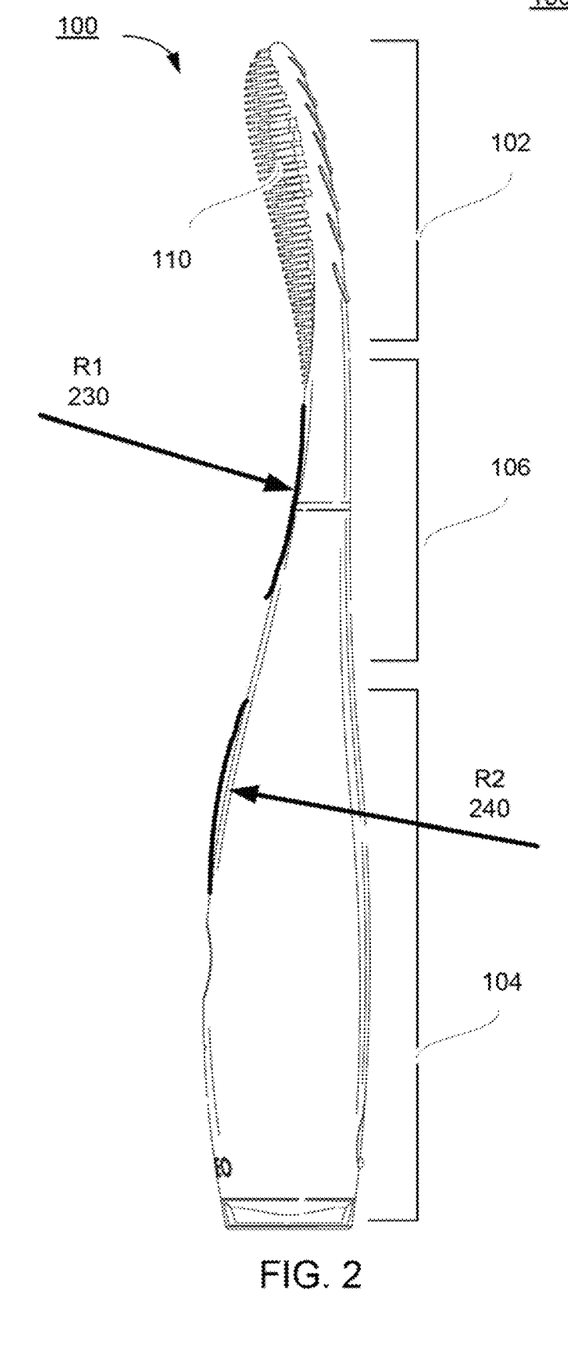
FIGS. 2 and 3 are side views of a toothbrush, according to one embodiment.
Figure 3:
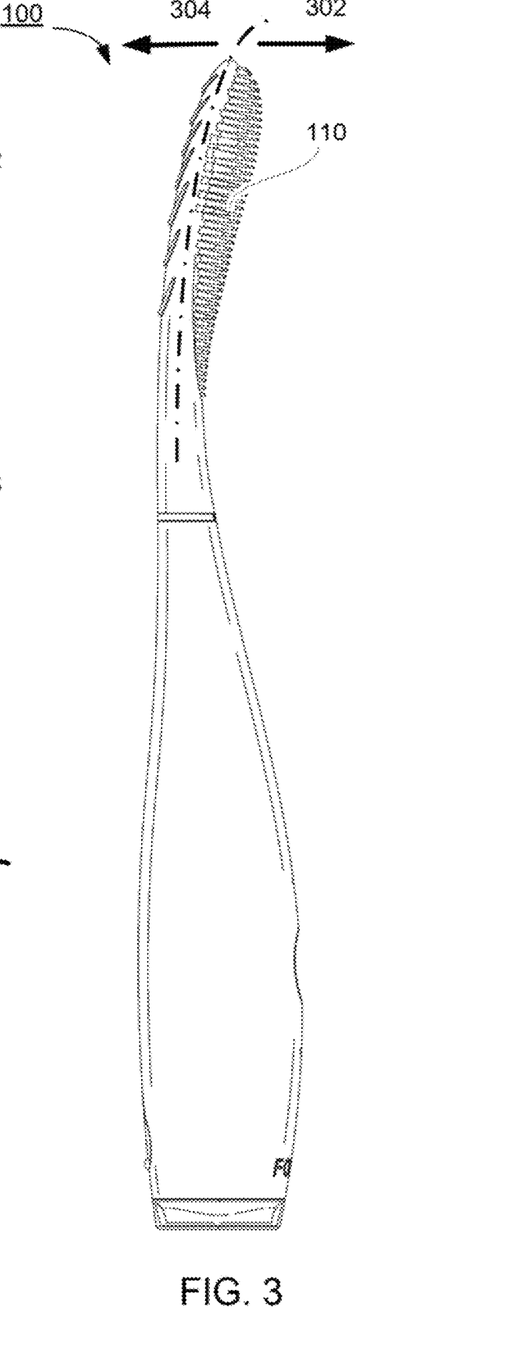

FIGS. 2 and 3 are side views of a toothbrush, according to one embodiment. In some embodiments, tooth brush 100 has an ergonomically designed shape. A curved and tapering shape of the head 102 facilitates comfortable usage inside the mouth. The handle 104 optionally has a smooth and arcuate surface that facilitates a comfortable and convenient hand grip and is well-contoured to the shape of the palm.

In some embodiments, the toothbrush surface can also be designed to contour to the curves of the mouth. In one embodiment, one or more surfaces of the toothbrush 100 are deformable or bendable. For example, if the textured surface is composed of silicone, the surface can compress or bend when pressed against an inner wall of the cheek or a gum or tongue surface to mold to the contour of the mouth part for providing a thorough cleansing and for better cleaning of mouth surfaces that are curved. In some embodiments, the head 102 is flexible and can bend along its length or at the neck 106 during usage to conform to the shape of the user's mouth. The brush head 102 can also be replaceable with new brush heads as desired. In some embodiments, all or substantially all of the toothbrush is covered with an outer layer of silicone or other polymer material. In the embodiment of FIG. 1, for example, only a base portion of the handle 104 at the bottom-most section is not covered with silicone and a portion at the neck 106 where the head is detachable from the neck (which can be composed of a metal accent) is not covered with silicone. In some embodiments, the tooth brush is completely waterproof In the FIG. 1 embodiment, the base portion of the handle is a clear/transparent or translucent band (e.g., plastic or other polymer) that includes a lighting mechanism nearby or above the band, the lighting mechanism allowing light to shine through such that a user can determine whether the device is turned on or off by whether there is light shining through the clear base band. The base allows the device to stand on a surface, such as a tabletop.

Furthermore, as shown in FIG. 2, in some embodiments, the neck 106 couples the handle 104 to the head 102 of the tooth brush 100 via a curved or arcuate surface that transitions smoothly from a handle-proximal region that is broader than a head-proximal region, to the head-proximal region. In such embodiments, a radius of curvature of the arcuate surface (e.g., R1 230 or R2 240, illustrated in FIG. 2) varies from approximately 5-20 centimeters (e.g., R2 240) at the broader handle-proximal region to approximately 5-10 centimeters (e.g., R1 230) at the narrower head-proximal region, for a 15 to 25 centimeter total length of tooth brush 100. Radii of curvature optionally scale linearly with dimensions such as a total length of tooth brush 100.

Additionally, as shown in FIGS. 2-3, in some embodiments, the bristle touch-points 110 vary in length from a first length at an apex of the head 102, to a second length (e.g., greater than the first length, for example, by a factor of 2-10) in a central region of the head 102 between the apex and a base of the head 102, to a third length (e.g., less than the second length, for example, by a factor of 2-10) at the base of the head 102. The varying length of the bristle-touch points allows for easier access to hard-to-reach sections of the mouth, such as molars, premolars, and other inner mouth parts. In some embodiments, for a 15 centimeter tooth brush length, the first length ranges from approximately 1 millimeter to 3 millimeters; the second length ranges from approximately 3 millimeters to 15 millimeters; and the third length ranges from approximately 1 millimeter to 3 millimeters. In some embodiments, a ratio of the second length to the first length ranges from approximately 2 to 10; a ratio of the second length to the third length ranges from approximately 2 to 10; and a ratio of a length of the tooth brush to the second length ranges from approximately 10 to 100.

FIG. 3 additionally illustrates, in the side view, a front surface 302 of the tooth brush head that includes the bristle touch-points 110 arranged along rows, and a back surface 304 of the tooth brush that comprises a plurality of ridges. In some embodiments, the touch-points may also vary in breadth and aspect ratio along the front surface 302 of the head 102. In some embodiments, the touch points 110 include at least two different types of touch-points (e.g., thicker and thinner). The touch points of a type can be grouped to provide a pattern. For example, a group of thicker touch points may be located at the apex of the head 102 and a group of thinner touch points toward a base of head 102. In some embodiments, at least 10%, 20%, 30%, 40%, 50% of the front surface 302 of head 102 includes touch points of a different type than the rest of the front surface of head 102.

In general, in some embodiments, a variety of other touch-point arrangements are possible—for example, thinner touch points at the top and thicker at the bottom, thinner on one side and thicker on the other side, alternating rows of thinner and thicker, various areas or groupings of thinner and thicker in different locations on the head 102, and so forth. In addition, different types of touch points can be included, such as taller or shorter touch points, touch points with more or less bulbous ends, touch points with ends of different shapes (e.g., pointed, feathered, ridged, etc.), and so forth. Similarly, the touch points can be arranged more or less densely, can be positioned on both the front and back of the tooth brush, can be otherwise located on the tooth brush (e.g., only in the middle, only at the edges, etc.), among other variations.

In some embodiments, the thinner touch points and thicker touch points may vary in size and spacing. In various embodiments, the thinner touch points are 25-80% thinner (e.g., 30%, 40%, 50%, 60%, 70%, etc. or values in between) compared to the thicker touch points. In various embodiments, the thinner touch points are spaced closer together (e.g., the distance between touch points) by 15%-60%.

Figure 4:
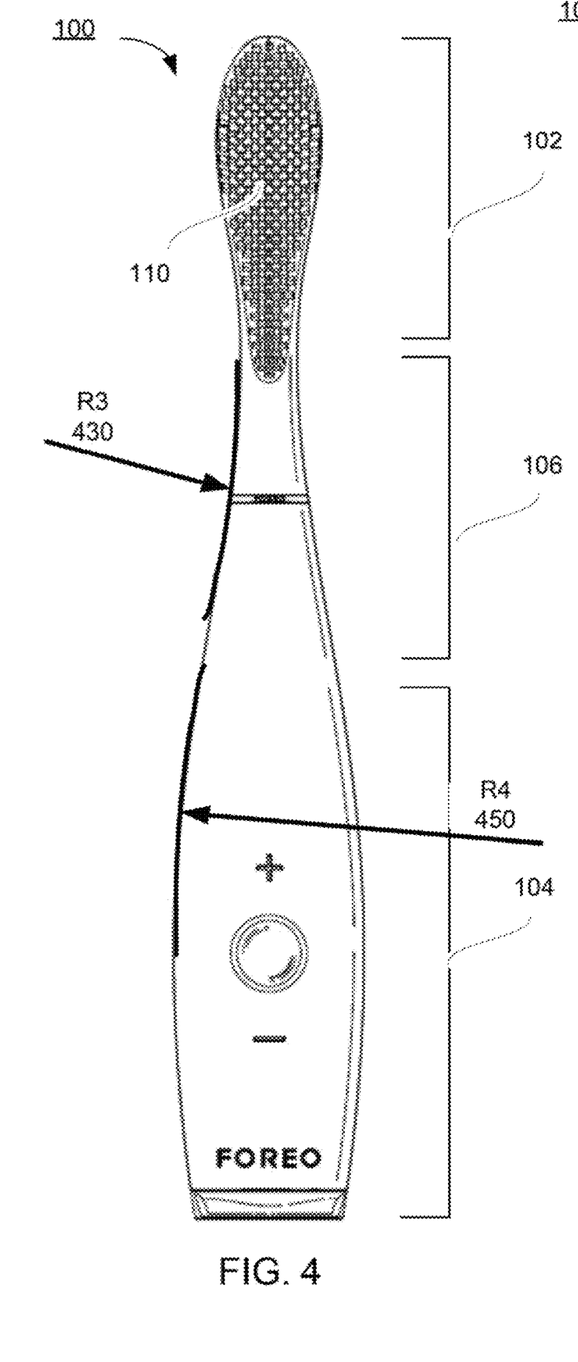
FIG. 4 is a front view a toothbrush, according to one embodiment.

FIG. 4 is a front view a toothbrush, according to one embodiment. In some embodiments, as shown in FIG. 4, bristle touch points 110 extend substantially to the edge of the toothbrush head 102. For example, the touch-points extend to within approximately 1 millimeter of a lateral periphery or edge of the front surface of the head 102. This configuration of touch points extending substantially to the lateral peripheries of the front surface of the head leave negligible area around the side of the brush when inserted into the mouth, thereby improving accessibility of the touch points to the hard-to-reach areas of the mouth without the wall of the head 102 hitting or touching the inside of the mouth.

As explained with reference to FIG. 2, the neck 106 couples the handle 104 to the head 102 of the toothbrush 100 via a curved or arcuate surface that transitions smoothly from a handle-proximal region that is broader than a head-proximal region, to the head-proximal region. In such embodiments, a radius of curvature of the arcuate surface (e.g., R3 430 or R4 450, illustrated in FIG. 4) varies from approximately 5-20 centimeters (e.g., R5 450) at the broader handle-proximal region to approximately 5-10 centimeters (e.g., R4 430) at the narrower head-proximal region, for a 15 to 25 centimeter total length of tooth brush 100. Radii of curvature optionally scale linearly with dimensions such as a total length of tooth brush 100.

Figure 5:
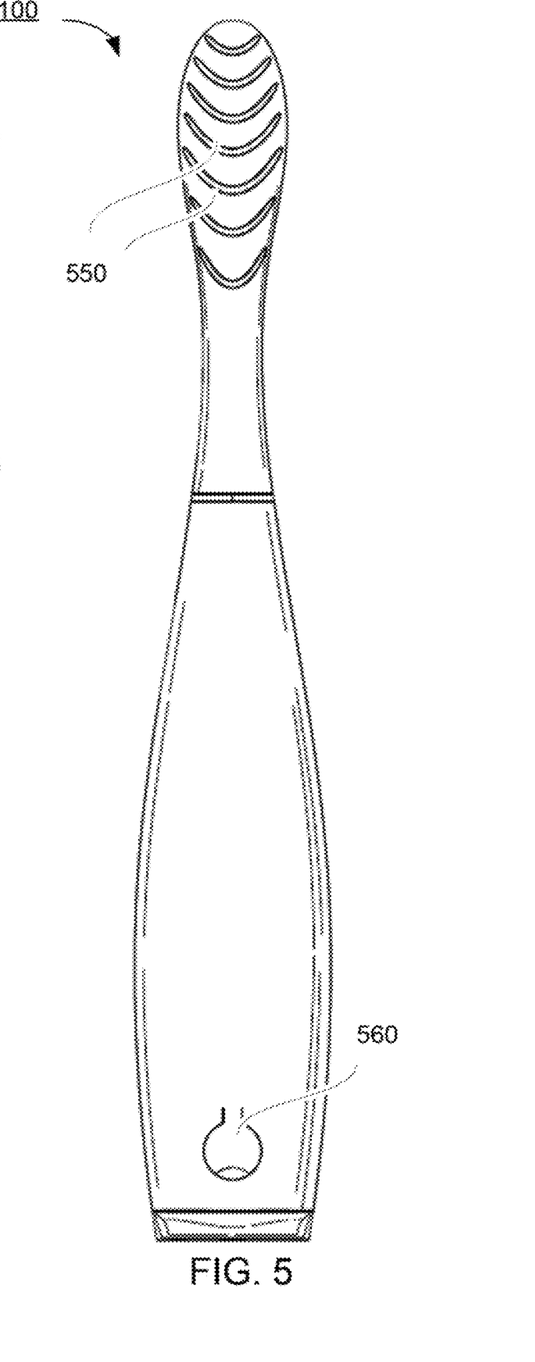
FIG. 5 is a back view a toothbrush, according to one embodiment.

FIG. 5 is a back view a toothbrush, according to one embodiment. Toothbrush 100 on a back side of the head 102, as shown in FIG. 5, includes a series of smooth silicone ridges 550 (e.g., arranged in an undulating or wave-like formation), intended to provide minimal abrasion and to maximize a mechanical pulsation energy transfer and the effectiveness of a dual-frequency (e.g., high-frequency and lower-frequency) toning and muscle-relaxing functions (e.g., at lower vibration frequencies). In some embodiments, more or fewer ridges, different patterns and configurations, different sizes and shapes, could be used. Furthermore, charger port 560 enables battery charging via various charging means, such as using AC mains, transformer or power converters, inductive charging, or any other suitable charging means. In other embodiments, a base with one or more recesses into which the toothbrush 100 can be positioned, and the toothbrush can be charged through the base, for example via inductive charging based on a transmitting coil in the base and a receiving coil in the toothbrush or via metal contacts in the base and toothbrush.

Figure 6:
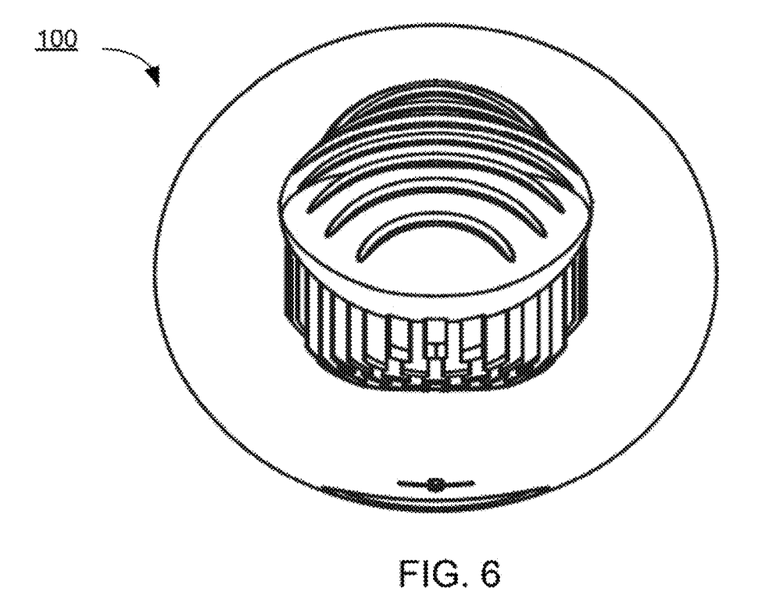
FIGS. 6 and 7 are top and bottom views of a toothbrush, respectively, according to one embodiment.
Figure 7:
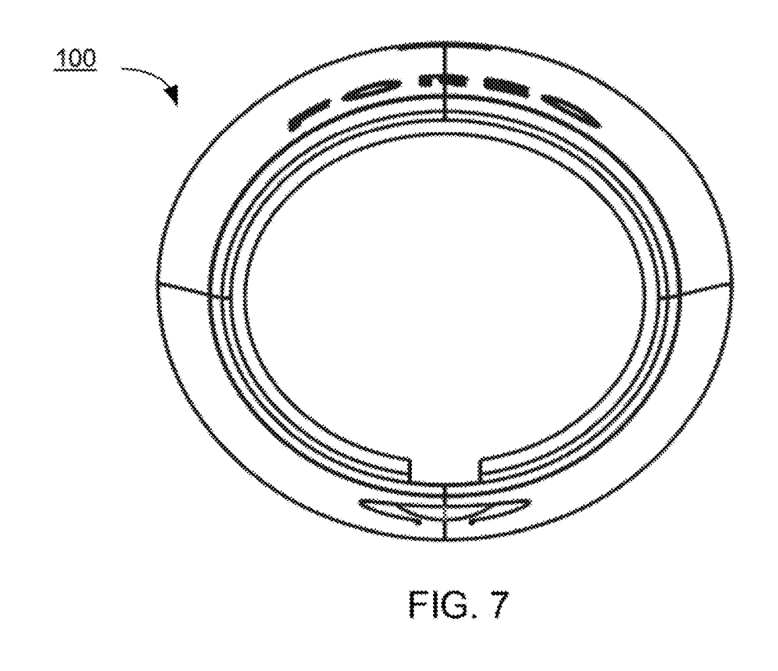
Figure 8:
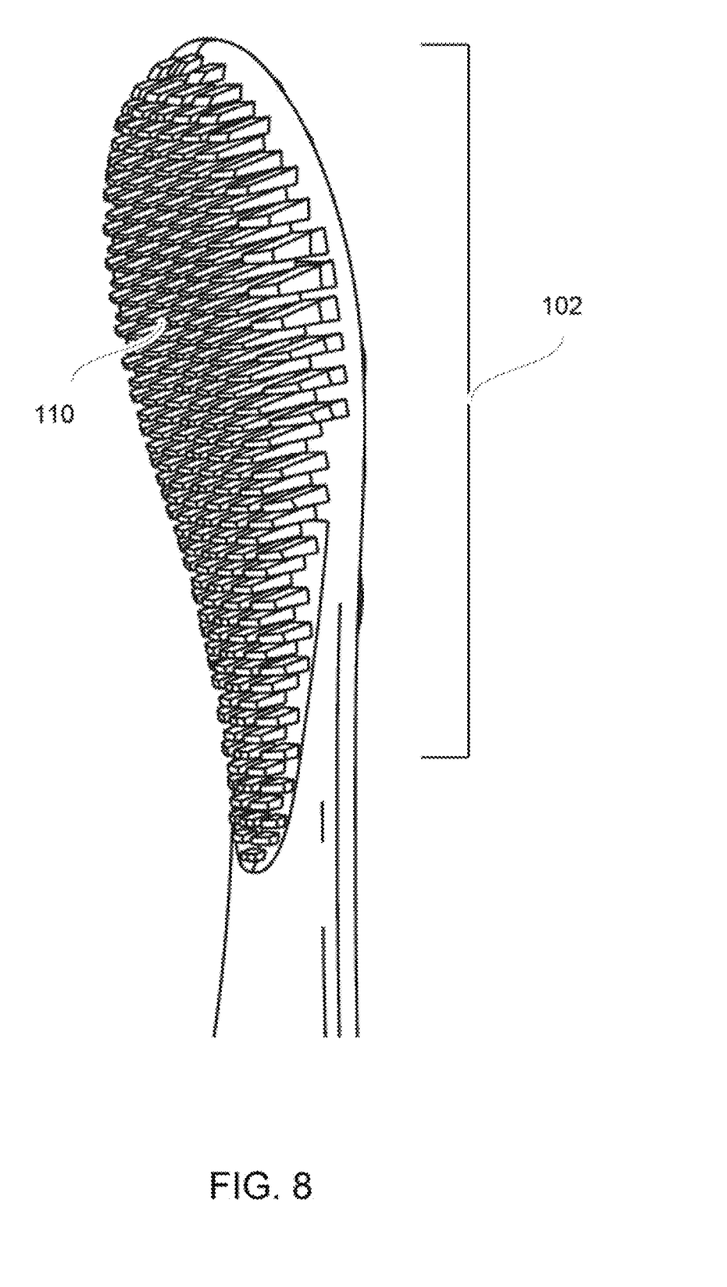
FIG. 8 is a perspective view of a head of a toothbrush, according to one embodiment.
Figure 9:
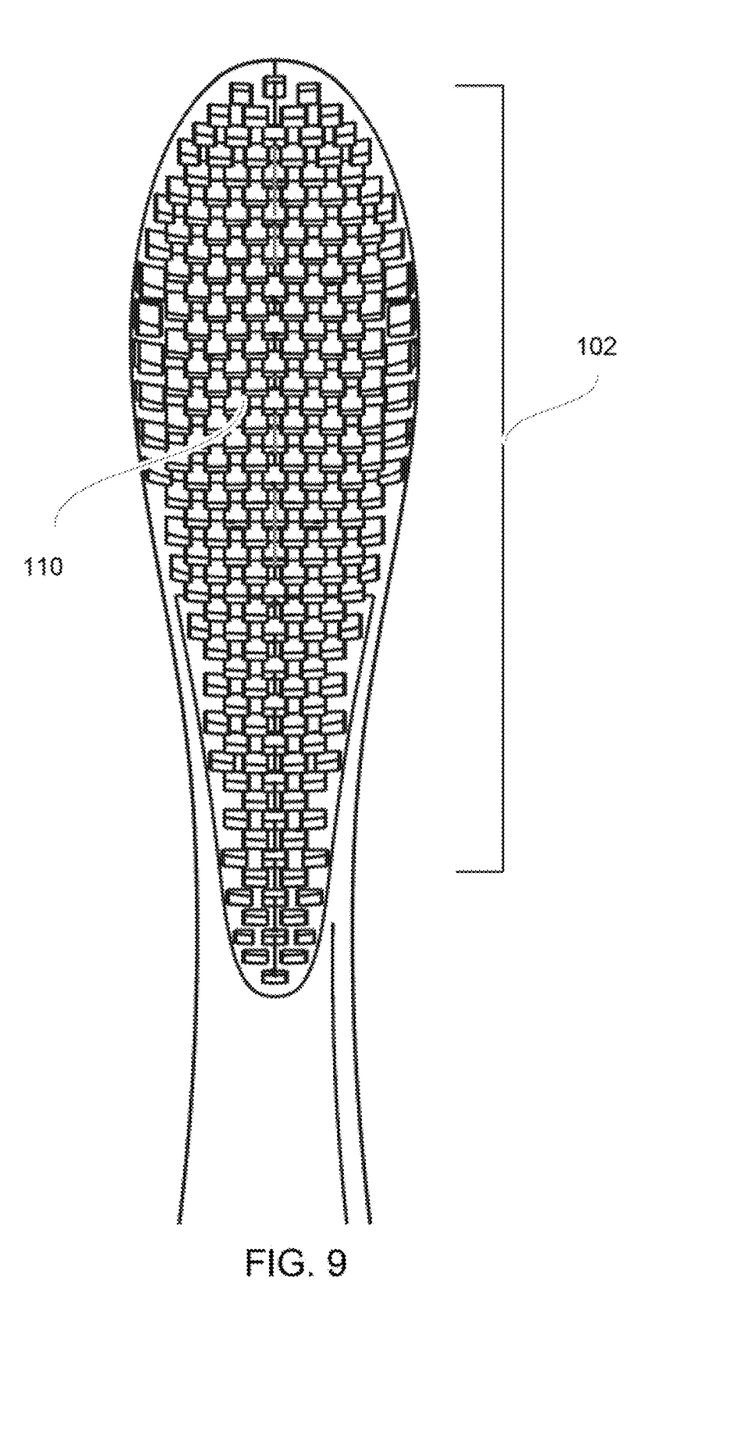
FIG. 9 is a front view of a head of a toothbrush, according to one embodiment.

FIGS. 6 and 7 include top and bottom views of toothbrush 100, according to one embodiment. FIG. 8 is a perspective view of a head of a toothbrush head, according to one embodiment. As explained with reference to FIGS. 2-3, and as shown in FIG. 8, in some embodiments, the bristle touch-points vary in length from a first length at an apex of the head 102, to a second length (e.g., greater than the first length) in a central region of the head 102 between the apex and a base of the head 102, to a third length (e.g., less than the second length) at the base of the head 102. FIG. 9 is a front view of a head of a toothbrush head, according to one embodiment. As shown in FIG. 9, in some embodiments, bristle touch-points along adjacent rows are mutually interleaved, thereby improving contact area with the teeth. As shown in FIG. 9, each horizontal row of bristle touch-points is offset from the row next to it such that the gap between two touch-points in one row aligns with a touch-point in the next row that stretches from one side of the gap to the other side of the gap. In other embodiments, the bristle touch-points can be non-interleaved or positioned in a single file line vertically and horizontally. Other patterns can also be used, including touch-points arranged diagonally or in circular patterns. Similarly, different patterns or arrangements can be used along different portions of the brush head 102. For example, an interleaved pattern might be used only on the top or bottom or middle portion, or only around the edges, or along one of the sides.

Figure 10:
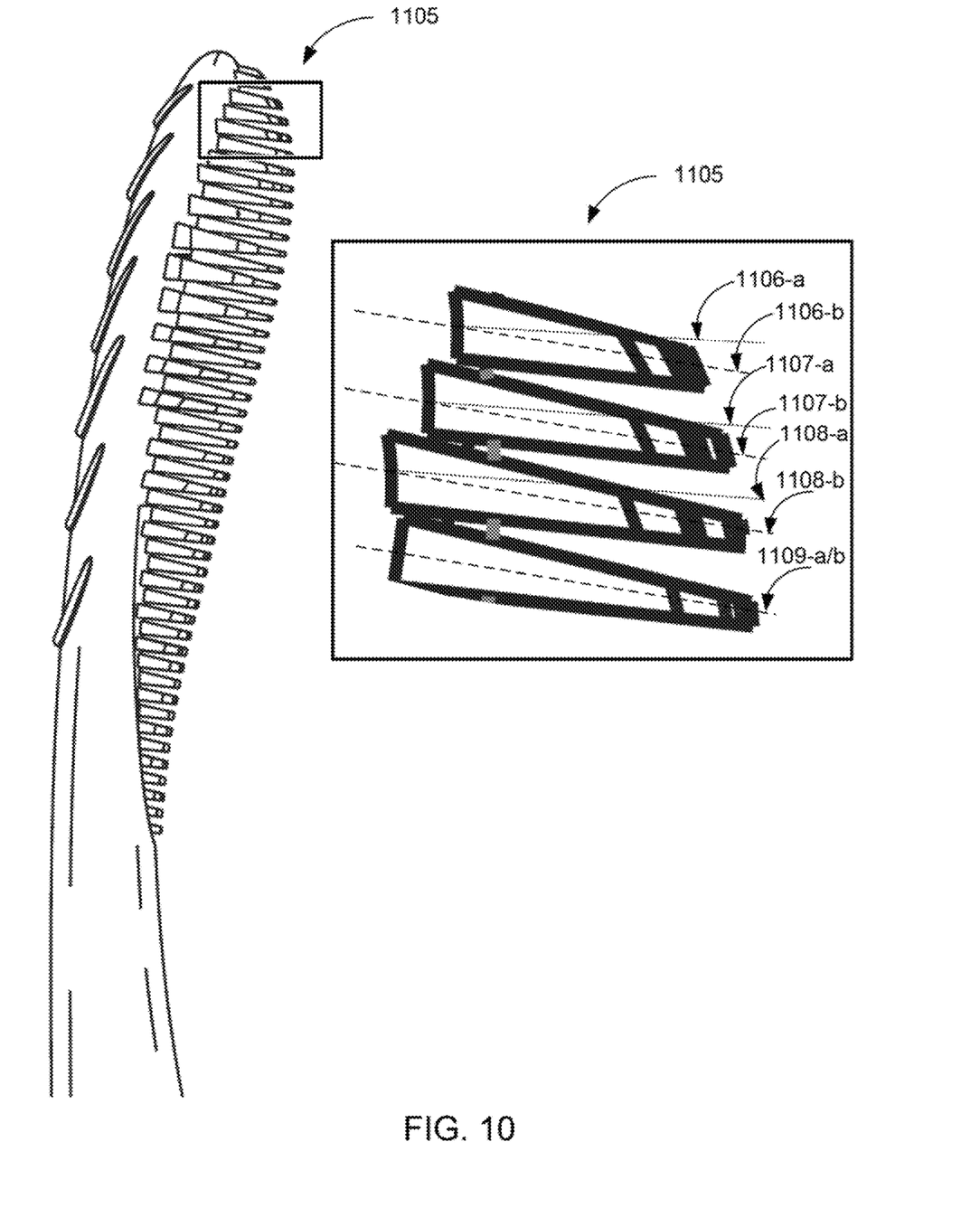
FIG. 10 is a side view of a head of a toothbrush, according to one embodiment.

FIG. 10 is a side view of a head of a toothbrush, according to one embodiment. FIG. 10 illustrates that the bristle touch-points can be of different lengths or heights, with some being longer and some being shorter, as explained above. For example, in FIG. 10, the touch-points at the middle portion of the brush are longer than the touch-points at the top or bottom of the brush. The touch points can also vary in thickness or other dimensions across the length or width of the brush head 102, as can be seen from FIG. 10. The inset 1105 of FIG. 10 provides another perspective of the centered, symmetric tapering of touch points versus the non-centered, asymmetric tapering. In some embodiments, as explained with reference to FIG. 1 above, a bristle touch-point may asymmetrically taper away from the central axis and the axis of tapering may be offset and angled (e.g., non-parallel) to the central axis of the touch-point. In this case, the central axis of the touch point is orthogonal to the plane of the base of the touch point where the touch point contacts or is attached to the head of the tooth brush. For example, in the illustration of inset 1105 of FIG. 10, the axes of tapering (e.g., 1106-*b*, 1107-*b*, 1108-*b*) for the touch points is distinct from, offset or at an angle to the central axes (e.g., 1106-*a*, 1107-*a*, 1108-*a*) of the touch-point as the touch-point tapers along its length. A measure of this angular separation between the axis of tapering and the central axis may vary from one touch point to another. In alternative embodiments, for some touch points, a center of the touch-point cross section may align with the central axis of the touch-point throughout the length of the touch-point (e.g., the central axis and the axis of tapering 1109-*a/b* coincide for the lower most touch point illustrated in the inset 1105)—in other words, the lowermost bristle touch point tapers along its central axis.

Figure 11A:
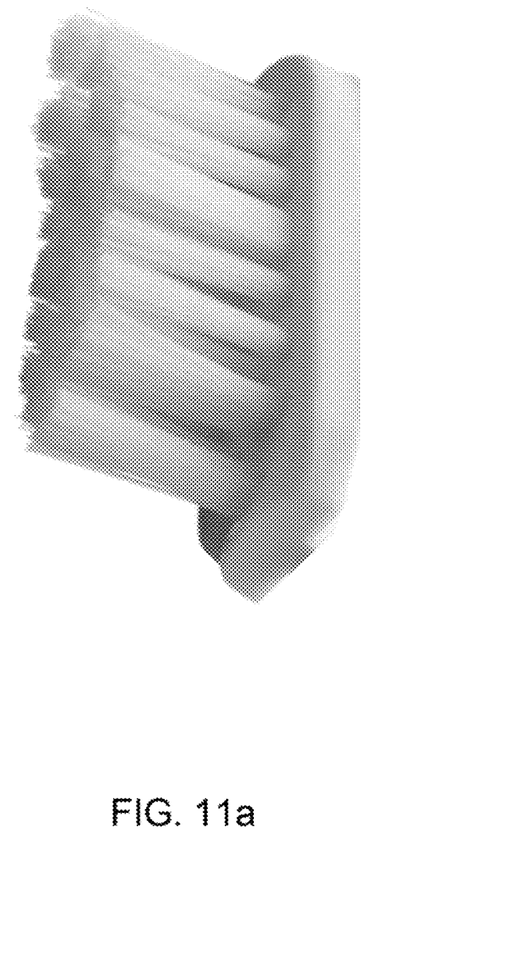
FIG. 11a is a perspective view of a convention toothbrush head.
Figure 11B:
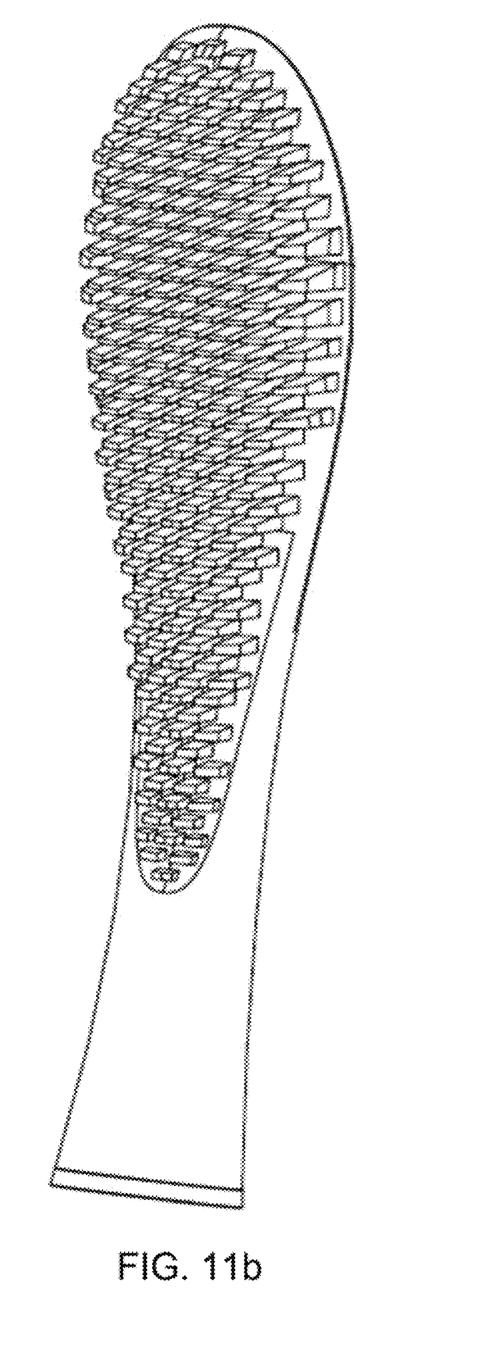
FIG. 11b is a perspective view of a toothbrush head, according to some embodiments.

FIG. 11*a* is a perspective view of a conventional toothbrush head. Traditional toothbrushes have bristle clusters, each bristle cluster having multiple narrow, filamental bristles made of a stiff material such as nylon (e.g., typically having a Young's modulus exceeding 1 GPa, such as in the 2-4 GPa range). Traditional bristles are frequently harsh on sensitive mouth parts due to the stiffer and narrower filamental bristles. In comparison, FIG. 11*b* is a perspective view of a toothbrush head, according to some embodiments of the instant disclosure. As described above, the individual bristle touch-points 110 are single solid elongate structures made from certain polymer materials (such as silicone). As a result, the bristle touch points 110 are gentler on the mouth parts and do not easily damage or injure the sensitive mouth parts (such as gums and other soft tissue of the mouth) during brushing or mechanical stimulation. Accordingly, the touch-points described herein are gentler than bristles used in conventional toothbrushes. This results in improved comfort and functionality for children, for people with sensitive teeth, for people with dental conditions such as receding gum lines, for aggressive brushers, and the like.

Figure 12:
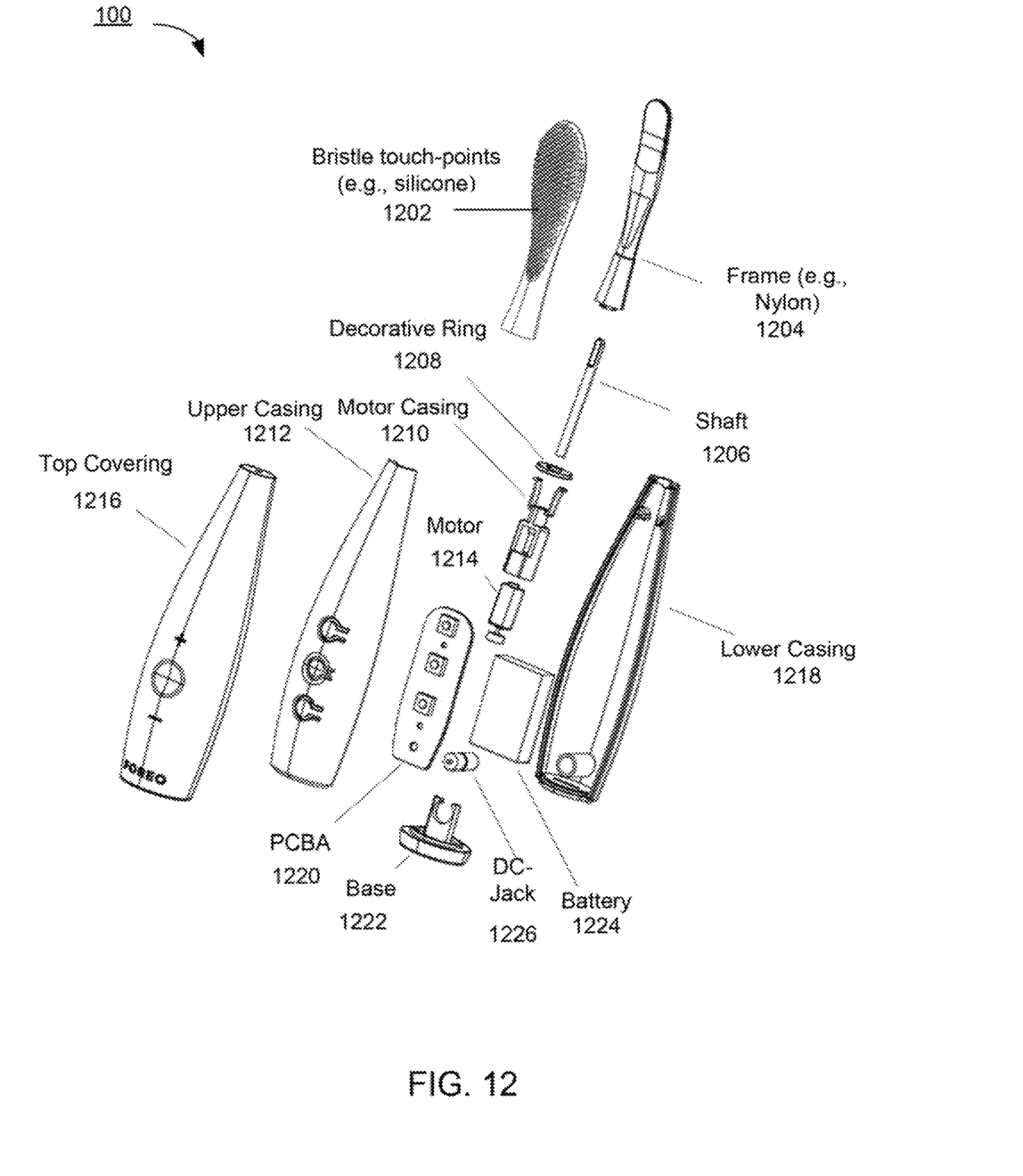
FIG. 12 is an exploded view of a toothbrush, according to one embodiment.

FIG. 12 is an exploded view of a toothbrush 100 illustrating various internal components of the tooth brush 100, according to one embodiment. As shown in FIG. 12, in some embodiments, the toothbrush 100 includes bristle touch-points 1202 (corresponding to touch points 110 explained with reference to FIG. 1) on the front side of the head, a frame 1204 (e.g., a nylon frame) on the back side of the head, and a shaft 1206 extending along at least a portion of the head and/or the neck. The shaft 1206, optionally couples to a ring 1208 and motor casing 1210. The ring 1208 can be a decorative ring at the neck, such as a metal component that separates the head from the rest of the toothbrush. Motor casing 1210 covers or encases one or more motors 1214 (corresponding to motor(s) 1308) explained further with reference to FIG. 13). As described with reference to FIG. 13, the motor(s) are operated on electric energy provided by battery 1224 and other electronic circuitry (such as a controller and so on) present on printed circuit board or PCBA 1220 (corresponding to battery and power supply 1304). A direct current or DC-jack 1226 also optionally couples to the motor electronics. A top covering 1216 (e.g., composed of silicone or other suitable material), upper casing 1212, and lower casing 1218 form the outer protective covers for the handle of the tooth brush. The casings 1212, 1218 are made of plastic or other suitable materials.

Figure 13:
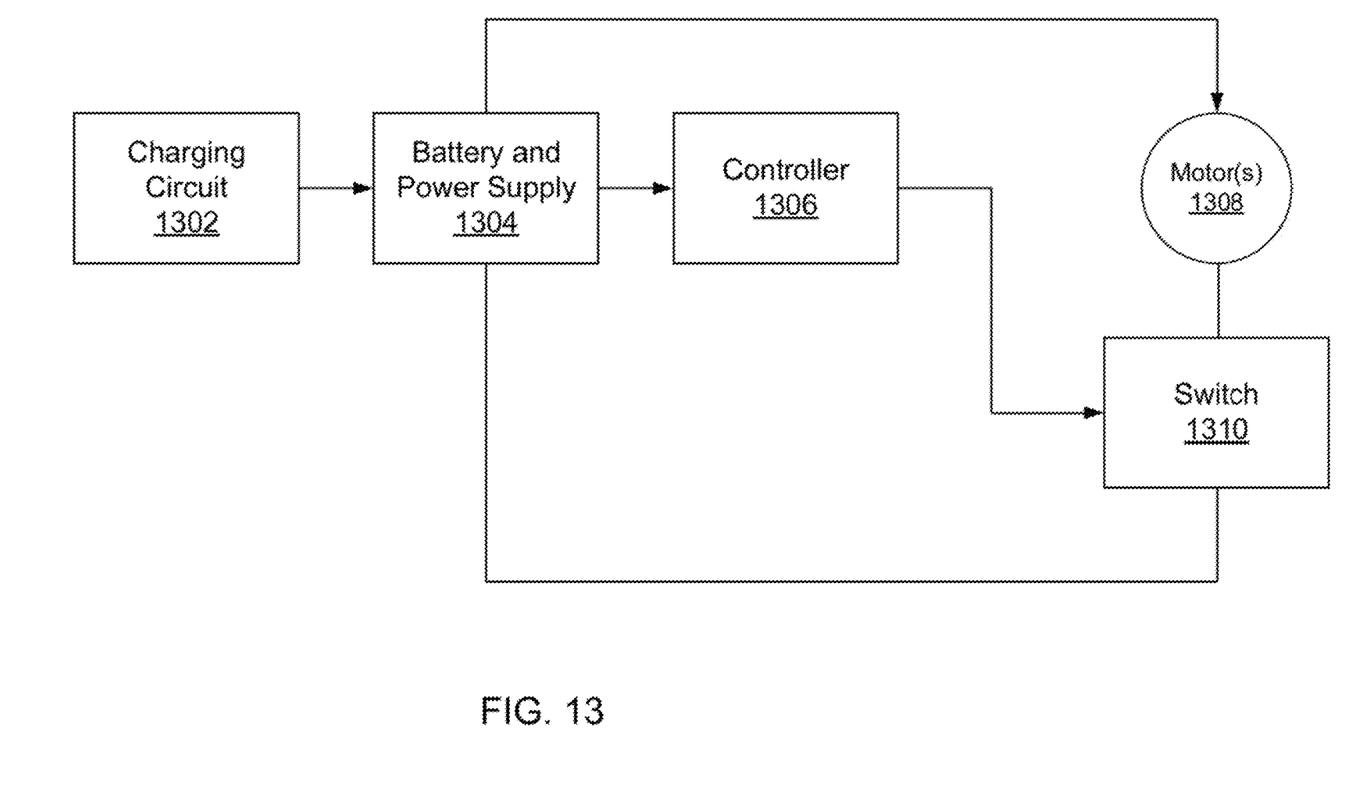
FIG. 13 is a graphical illustration of internal components of a toothbrush, according to one embodiment.

FIG. 13 is a graphical illustration of internal components of a toothbrush, according to one embodiment. In one embodiment, the touch points 110 of the tooth brush 100 are configured to vertically oscillate from the tooth brush to the mouth parts to create a tapping motion in the mouth. The vertical tapping in the mouth in this embodiment provides a gentle cleansing of the surface being tapped on (e.g., teeth, gums, tongue, inner cheek tissue, and the like), as opposed to a rotating or translational motion that can cause a less favorable twisting or stretching of the tissue that may cause damage to or scratching of the tissue surface.

The vertical tapping motion can be generated by the vibrations of one or more motors 1308, or other electromagnetic device in the brush, by electromechanical mechanisms, among other means. For example, the motors 1308 can be positioned in the brush to cause the vertical oscillations of the touch points, such as by positioning one or more motors 1308 directly under or adjacent to the bristle touch points. The oscillation of the motor(s) 1308 can cause one or more of the touch points to move orthogonal to the mouth's surface to tap the inner mouth. Multiple motors 1308 can be arranged near the head 102 of the tooth brush 100 to create different motions or different speeds of vertical oscillations. For example, the motors 1308 can be positioned so that different touch point arrangements or patterns on the textured surface can oscillate differently from one another to provide one type of tapping motion for some touch points and a different type (e.g., different speed, pattern, etc.) for other touch points.

In some embodiments, a high-, or low-frequency motor creates pulsations that vibrate the tooth brush 100. A high frequency oscillating motor may provide vibrations between 50 and 300 Hz; and a low frequency oscillating motor in the 50-130 Hz range. Pulsation frequencies higher and lower than this range may also provide beneficial cleansing of inner mouth surface or tissue. Frequencies in this range typically provide improved cleansing and the stimulation of blood circulation and lymph flow within the mouth. In some embodiments, the high-, or low-frequency motors can be used in an alternating fashion to provide alternating low and high frequency pulsations to the tooth brush 100.

The one or more motors 1308 are enclosed in within the toothbrush 100, which is enclosed by one or more casings including an upper casing 1212 and a down casing 1218 (see FIG. 12), made of a suitable material, such as plastic. A controller 1306, provides control to the one or more motors 1308, which is powered by a battery and power supply 1304. The battery is charged via a charging circuit 1302 through a charging port, such as a charging port 560 (see, FIG. 5). The controller 1306 enables or disables power supply from the battery 1304 to the motor(s) 1308 via actuation of the switch 1310 in pulses of specified pulse duration period based on levels of the power supply voltage, thereby controlling the rotational operation of the motor(s) 1308.

Summary

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention.

What is claimed is:

1. A tooth brush device, comprising:
a head comprising an apex, a base opposite the apex, a front surface with bristle touch-points and a back surface, the bristle touch-points arranged along rows, the rows orthogonal to a longitudinal axis of the head extending from the apex of the head to the base of the head, each of a plurality of the bristle touch-points being a single solid elongate structure extending from the head;
a shaft extending along at least a portion of the head;
a neck that couples the handle to the head;
a motor casing coupled to the shaft; and
a motor encased in the motor casing that is configured to create vibrations within the head of the toothbrush;
wherein the apex, base, front surface, bristle touch-points, back surface, and at least a portion of the neck comprise a single piece of polymer material.

2. The tooth brush device of claim 1, wherein the motor is configured to create a vertical tapping motion of the bristle touch-points.

3. The tooth brush device of claim 1, wherein the motor and the motor casing are disposed between an upper casing and a lower casing.

4. The tooth brush device of claim 3, wherein the upper casing and lower casing are made of plastic.

5. The tooth brush device of claim 4, further comprising a top covering coupled to the upper casing.

6. The tooth brush device of claim 5, wherein the top covering comprises the same polymer material as the front surface and the back surface of the head.

7. The tooth brush device of claim 6, wherein the polymer material comprises silicone.

8. A tooth brush device, comprising:
a head comprising an apex, a base opposite the apex, a front surface with bristle touch-points and a back surface, the bristle touch-points arranged along rows, the rows orthogonal to a longitudinal axis of the head extending from the apex of the head to the base of the head, each of a plurality of the bristle touch-points being a single solid elongate structure extending from the head;
a handle comprising an upper casing, a lower casing, and a top covering, the top covering coupled to the upper casing and comprising the same material as the front surface and back surface of the head;
a neck that couples the handle to the head;
a shaft extending along at least a portion of the head and at least a portion of the neck;
a motor casing coupled to the shaft and disposed between the upper casing and the lower casing of the handle; and
motor encased in the motor casing that is configured to create vibrations within the head of the toothbrush;
wherein the apex, base, front surface, bristle touch-points, back surface, and at least a portion of the neck comprising a single piece of polymer material.

9. The tooth brush device of claim 8, wherein each of a first plurality of the bristle touch-points has a substantially rectangular cross-section.

10. The tooth brush device of claim 9, wherein each of a second plurality of the bristle touch-points has a substantially trapezoidal cross-section.

11. The tooth brush device of claim 10, wherein each of the first plurality of bristle touch-points having a substantially rectangular cross-section is disposed closer to a center of the front surface of the head than is each of the second plurality of bristle touch-points having a substantially trapezoidal cross-section.

12. The tooth brush of claim 8, wherein the neck couples the handle to the head via an arcuate surface that transitions smoothly from a handle-proximal region that is broader than a head-proximal region.

13. The tooth brush device of claim 8, further comprising a decorative ring coupled to and disposed about the shaft.

14. The tooth brush of claim 8, wherein the head is flexible and can bend along its length.

15. The tooth brush device of claim 14, wherein the polymer material comprises silicone.

16. The tooth brush of claim 15, wherein the back surface defines a series of smooth ridges.

17. A tooth brush device, comprising:
a head comprising an apex, a base opposite the apex, a front surface with bristle touch-points and a back surface, the bristle touch-points arranged along rows, the rows orthogonal to a longitudinal axis of the head extending from the apex of the head to the base of the head, each of a plurality of the bristle touch-points being a single solid elongate structure extending from the head;
a handle comprising an upper casing, a lower casing, a top covering, and a base, the top covering coupled to the upper casing and comprising the same material as the front surface and back surface of the head;
a neck that couples the handle to the head;
a shaft extending along and disposed within at least a portion of the head and at least a portion of the neck;
a decorative ring coupled to and disposed about the shaft;
a motor casing coupled to the shaft and disposed between the upper casing and the lower casing of the handle; and
a motor encased in the motor casing that is configured to create vibrations within the head of the toothbrush;

wherein the apex, base, front surface, bristle touch-points, back surface, and at least a portion of the neck comprise a single piece of polymer material; and wherein the polymer material comprises silicone.

* * * * *